US005873872A

United States Patent [19]

Thibault et al.

[11] Patent Number: 5,873,872

[45] Date of Patent: Feb. 23, 1999

[54] MULTIPOSITIONAL RESEALABLE VIAL CONNECTOR ASSEMBLY FOR EFFICIENT TRANSFER OF LIQUID

[75] Inventors: Jean Claude Thibault, Saint Egreve; Hubert Jansen, Haute Jarrie, both of France

[73] Assignee: Becton Dickinson and Company, Franklin Lakes, N.J.

[21] Appl. No.: 714,874

[22] Filed: Sep. 17, 1996

[51] Int. Cl.[6] .......... A61B 19/00

[52] U.S. Cl. .......... 604/414; 604/415; 604/412; 604/411; 604/403

[58] Field of Search .......... 604/283, 403, 604/411–416, 905, 404, 410

[56] References Cited

U.S. PATENT DOCUMENTS

| | | | |
|---|---|---|---|
| 2,607,503 | 8/1952 | Sonnenberg | 215/38 |
| 2,953,132 | 9/1960 | Richter et al. | 128/272 |
| 3,164,303 | 1/1965 | Trautmann | 222/190 |
| 3,206,080 | 9/1965 | Scislowicz | 222/383 |
| 3,356,093 | 12/1967 | Monahon | 128/349 |
| 3,357,427 | 12/1967 | Wittke et al. | 128/235 |
| 3,674,028 | 7/1972 | Ogle | 128/272 |
| 3,779,371 | 12/1973 | Rovinski | 206/47 |
| 3,838,689 | 10/1974 | Cohen | 128/218 |
| 4,020,839 | 5/1977 | Klapp | 128/272 |
| 4,210,255 | 7/1980 | Pan | 220/209 |
| 4,412,623 | 11/1983 | Schmidt | 215/11 R |
| 4,576,211 | 3/1986 | Valentini et al. | 141/329 |
| 4,672,996 | 6/1987 | Floyd et al. | 137/522 |
| 4,792,053 | 12/1988 | Towns et al. | 215/250 |
| 4,822,351 | 4/1989 | Purcell | 604/411 |
| 4,834,149 | 5/1989 | Fournier et al. | 141/1 |
| 4,834,152 | 5/1989 | Howson et al. | 141/286 |
| 4,884,703 | 12/1989 | O'Meara | 215/6 |
| 4,909,290 | 3/1990 | Coccia | 141/329 |
| 5,006,118 | 4/1991 | Yule | 604/408 |
| 5,088,996 | 2/1992 | Kopfer et al. | 604/415 |
| 5,171,214 | 12/1992 | Kolber et al. | 604/82 |
| 5,217,433 | 6/1993 | Bunin | 604/89 |
| 5,232,109 | 8/1993 | Tirrell et al. | 215/247 |
| 5,291,991 | 3/1994 | Meyer | 206/221 |
| 5,348,548 | 9/1994 | Meyer et al. | 604/403 |
| 5,352,196 | 10/1994 | Haber et al. | 604/90 |
| 5,358,501 | 10/1994 | Meyer | 604/415 |
| 5,360,413 | 11/1994 | Leason et al. | 604/249 |
| 5,385,546 | 1/1995 | Kriesel et al. | 604/85 |
| 5,423,791 | 6/1995 | Barlett | 604/403 |
| 5,425,465 | 6/1995 | Healy | 215/355 |
| 5,429,256 | 7/1995 | Kestenbaum | 215/247 |
| 5,487,737 | 1/1996 | Meyer | 604/403 |
| 5,494,170 | 2/1996 | Burns | 215/247 |
| 5,533,994 | 7/1996 | Meyer | 604/416 |
| 5,566,729 | 10/1996 | Grabenkort et al. | 604/905 |
| 5,598,939 | 2/1997 | Watson et al. | 215/307 |
| 5,613,291 | 3/1997 | Solomon et al. | 29/458 |
| 5,620,434 | 4/1997 | Brony | 604/411 |
| 5,685,845 | 11/1997 | Grimard | 604/82 |
| 5,702,019 | 12/1997 | Grimard | 215/301 |

FOREIGN PATENT DOCUMENTS

| | | |
|---|---|---|
| 0 406 374 B1 | 1/1991 | European Pat. Off. . |
| 1071487 | 9/1954 | France . |
| 1487413 | 7/1967 | France . |
| 2 738 550 | 3/1997 | France . |
| A 61 M 5/14 | 3/1987 | Germany . |
| 501 172 | 2/1971 | Switzerland . |
| WO 95/03841 | 2/1995 | WIPO . |

*Primary Examiner*—Robert A. Clarke
*Assistant Examiner*—David J. Cho
*Attorney, Agent, or Firm*—Allen W. Wark

[57] ABSTRACT

A connector assembly is provided for efficient flow of liquid into and/or out of a vial, such as a vial containing a lyophilized drug. The connector assembly includes a spike slidably mounted in the open top of the vial. The connector assembly further includes a stopper sealingly engaged in the open top of the vial and slidably moveable in response to the axially movement of the spike. Thus, movement of the spike relative to the vial will move the stopper into or out of sealing engagement with the vial. The connector assembly further includes a spring for generating a small amount of axial movement of the spike after the stopper has been moved into the opened position in the vial. Movement of the spike generated by the spring will cause a sufficient change in pressure to overcome surface tension and initiate an efficient flow of fluid into or out of the vial.

6 Claims, 7 Drawing Sheets

MULTIPOSITIONAL RESEALABLE VIAL CONNECTOR ASSEMBLY FOR EFFICIENT TRANSFER OF LIQUID

BACKGROUND OF THE INVENTION

1. Field of the Invention. The subject invention relates to a connector assembly for a vial, and more particularly, to a multipositional resealable vial connector that enables an efficient transfer of liquid into or out of the vial.

2. Description of the Prior Art. Many drugs are presented in dry form to achieve a longer shelf life. One type of dry drug is a lyophilized drug. A selected dose of a lyophilized drug may be stored in a glass vial that is sealed to prevent deterioration or contamination of the drug. A liquid solvent may be mixed with the lyophilized drug shortly prior to use, and the drug solution may be administered to a patient.

Some prior art vials of lyophilized drugs are sealed with a membrane that can be pierced by a needle or spike for delivering the liquid solvent into the vial and for subsequently administering the drug solution to a patient. It has been found, however, that fragments of the membrane can separate when the seal is being pierced, and thus inadvertently can be administered to a patient with the drug solution.

Other prior art vials include a rubber stopper that is urged into the vial by the spike, needle or other tubular structure that delivers the solvent to the vial. These stoppers cannot be conveniently accessed after they have fallen into the vial for reliably resealing the vial of drug solution. However, the loose stopper can unintentionally block the vial opening to impede the outflow of drug solution.

A very effective vial connector assembly is shown in U.S. Pat. No. 5,358,501 which issued to Gabriel Meyer on Oct. 25, 1994. Certain embodiments of the assembly shown in U.S. Pat. No. 5,358,501 include a tube with a proximal end in the vial and a distal end externally of the vial. First and second channels extend axially through the tubes. The first channel terminates at a first orifice at the extreme proximal end of the tube. The second channel terminates at a second orifice disposed distally of the first orifice. Portions of the tube defining the first orifice prevent the stopper from blocking the second orifice. Hence a drug solution in the vial can be completely emptied for administration to a patient. Other embodiments shown in U.S. Pat. No. 5,358,501 attach the stopper to the tubular structure that urges the stopper into the vial. Thus, the stopper does not fall to the bottom of the vial. This enables the vial to be re-sealed and further prevents the stopper from inadvertently falling into a position where the stopper can impede the flow of drug solution from the vial.

In many situations it is desirable to utilize a pointed spike on the vial connector to access a supply of solvent in a rigid container. It has been found that surface tension at the gas/liquid interface and a pressure differential between the vial and the container of solvent prevents the initial flow of solvent into the vial. Similar problems with pressure differential and surface tension may occur when the drug solution is being delivered from the vial. Where the container is a flexible container, such as a flexible infusion bag, it may be possible to squeeze the infusion bag to initiate fluid flow. However, if the container is rigid, this approach is not possible. Some medical practitioners overcome this problem by shaking the vial after it has been connected to the supply of solvent. However, this shaking can inadvertently separate the vial from the supply of solvent and can lead to a loss or contamination of the drug or drug solution. Furthermore, shaking an assembly with a pointed implement is an unsafe practice.

SUMMARY OF THE INVENTION

The subject invention is directed to a connector for use with a vial. The vial includes a bottom wall and an upstanding side wall. A shoulder extends inwardly from the top end of the side wall and a tubular neck extends upwardly from the shoulder to an open top. An annular rim may extend around portions of the neck that define the open top. Portions of the vial between the tubular neck and the bottom wall define an enclosure in which a lyophilized drug or a drug solution may be stored.

The connector of the subject invention includes a mounting collar mounted to and surrounding the open top of the vial. The collar is configured for sliding action, respective of the open top of the vial. To this end, the collar features a pair of opposed proximal and distal ends. A plurality of deflectable latches are disposed adjacent the proximal end end and dimensioned to engage the annular rim surrounding the opening top of the vial. A plurality of locking detents are provided intermediate the proximal and distal ends of the collar. The collar is slidable between an extreme distal position and an extreme proximal position respective of the open top of the vial. Moreover, once slid to its extreme proximal position, the collar can be slid in a distal direction to a third position intermediate the extreme proximal and extreme distal positions.

The connector further includes an elongate transfer tube mounted to the collar for movement between proximal and distal positions in the neck of the vial. The transfer tube includes a proximal end disposed within the vial and a distal end projecting from the vial. The distal end may be pointed sufficiently to pierce through a seal on a separate fluid container, such as a rigid container. The proximal end of the transfer tube includes mounting structure for engagement with a stopper. Portions of the transfer tube intermediate the proximal and distal ends include apertures for permitting transverse flow of fluid into or out of at least one of the channels passing axially through the transfer tube. A secondary seal is disposed on the transfer tube at a location distal from the apertures.

The stopper is secured to the mounting structure on the proximal end of a transfer tube. The stopper is dimensioned to sealingly engage the inner surface of the neck of the vial when the transfer tube is in its extreme distal position relative to the neck. Proximal movement of the transfer tube urges the stopper proximally beyond the neck of the vial and places the transverse apertures through the transfer tube in communication with interior portions of the vial. The secondary seal remains disposed in the neck of the vial so as to isolate a drug held within the vial from potentially contaminating contact with the ambient environment.

In use, a dry drug such as a lyophilized drug is stored in the vial and is protectively sealed by the stopper and the secondary seal. Solvent may be added to the lyophilized drug in the vial by placing the distal end of the transfer tube into communication with a container of solvent. The collar, together with the transfer tube, are then urged proximally relative the vial, such that the stopper secured to the proximal end of the transfer tube moves proximally in the neck of the vial. As the transfer tube approaches its extreme proximal position, the stopper will clear the neck of the vial to enable fluid communication between the container of solvent and the vial. More particularly, a clear path for fluid communication will be defined by at least one of the channels extending axially through the transfer tube and the transverse apertures disposed distally of and adjacent to the stopper.

As noted above, surface tension and pressure differentials between the vial and the supply of solvent often impede an efficient flow of solvent into the vial. In the prior art, this problem had been addressed by shaking the vial, the connector assembly and container of fluid to initiate flow. This prior art shaking was undesirable for reasons explained above. The connector of the subject invention overcomes the problems caused by surface tension and pressure differentials, and generates a rapid flow of liquid into the vial. More particularly, the transfer tube will move proximally relative to the vial in response to forces supplied by the health care worker attempting to add solvent to the dry drug. After the transfer tube reaches its extreme proximal position, the healthcare worker can alternately move the transfer tube between its extreme proximal position and the secondary position intermediate the extreme proximal and distal positions. This movement of the transfer tube relative to the vial is sufficient to overcome surface tension and to generate a favorable pressure differential that will generate immediate flow of liquid through the transfer tube and into the vial.

DETAILED DESCRIPTION OF THE PREFERRED EMBODIMENTS

Figure 1:
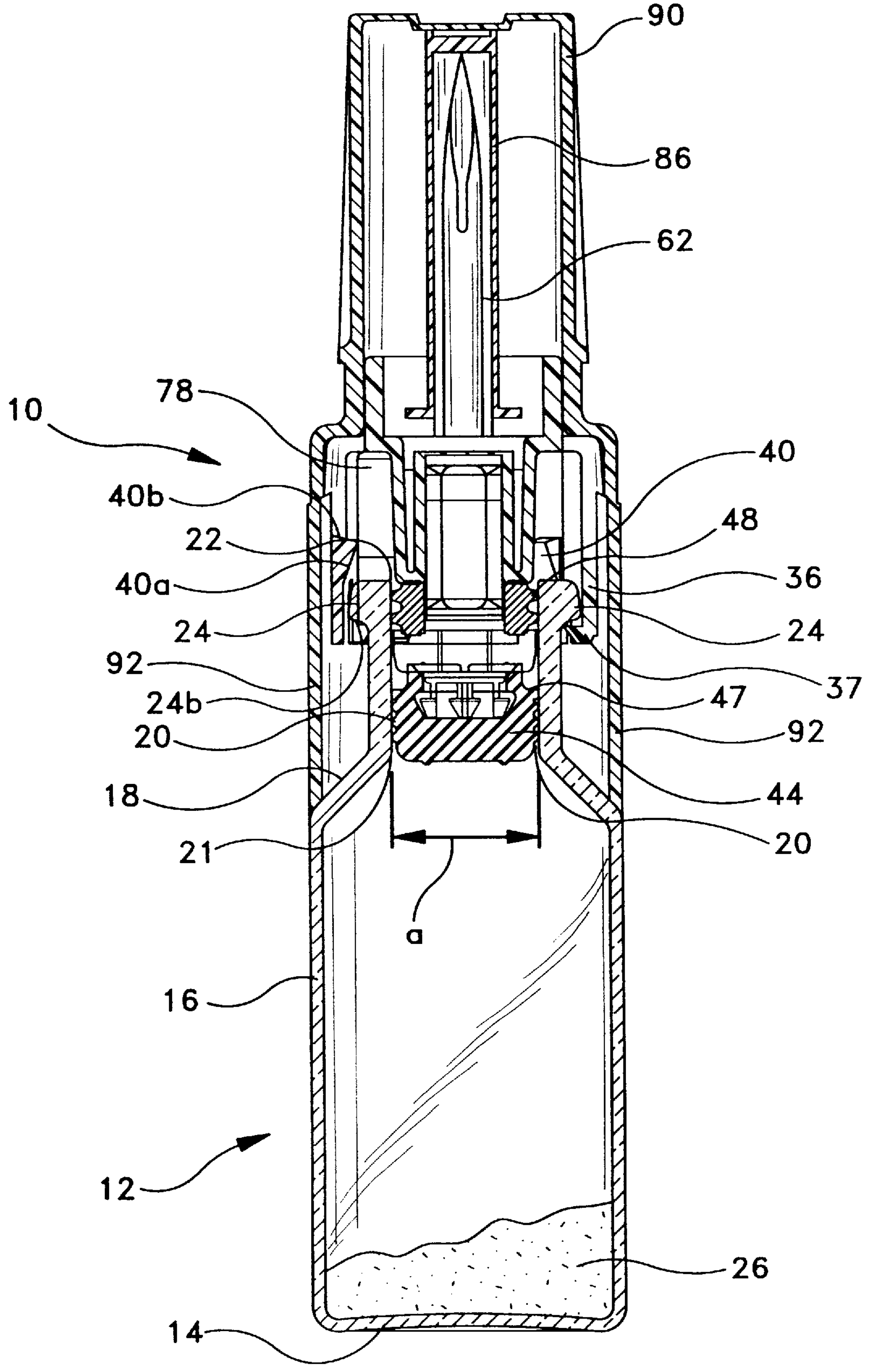
FIG. 1 is a longitudinal cross-sectional view of a connector assembly in accordance with the subject invention mounted to a vial.

A connector assembly in accordance with the subject invention is identified generally by the numeral 10 in FIGS. 1 and 3–6. The connector assembly 10 is used with a glass vial 12 having a bottom wall 14, a cylindrical side wall 16 extending upwardly from bottom wall 14, a shoulder 18 extending inwardly and upwardly from the end of cylindrical side wall 16 remote from bottom wall 14 and a cylindrical neck 20 of inside diameter "a" extending upwardly from shoulder 18. Neck 20 terminates at an open top 22. Top 22 is characterized by an annular rim 24 objecting outwardly thereabout.

Vial 12 is generally provided with a dry drug such as a lyophilized drug 26 stored therein. Connector assembly 10 functions to safely seal lyophilized drug 26 in vial 12 and to permit a solvent to be added to vial 12 for mixing with lyophilized drug 26 and forming a drug solution. Connector 10 further enables delivery of the drug solution to an IV set for administration to a patient.

Figure 3:
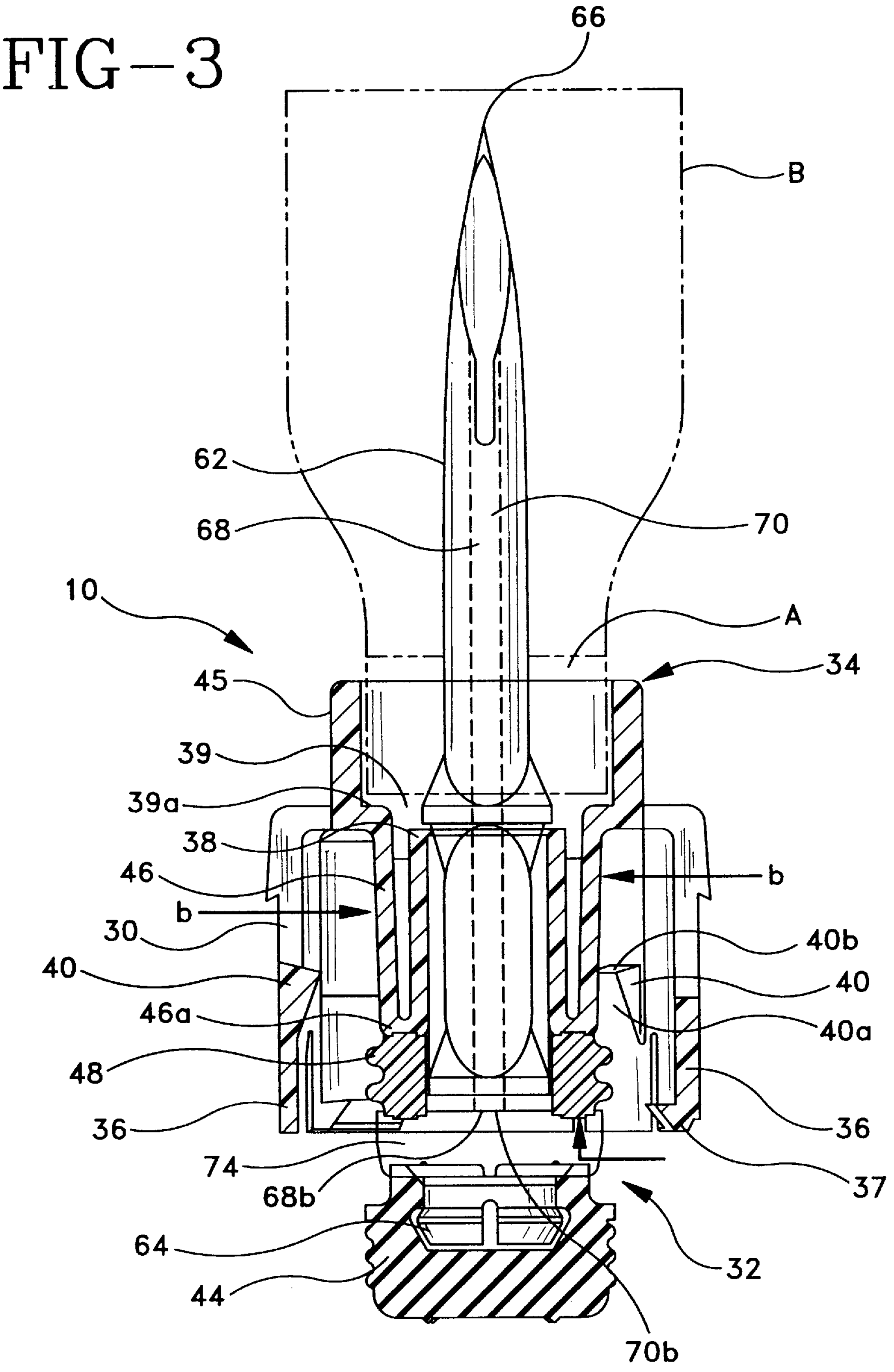
FIG. 3 is a detailed cross-sectional view of the connector assembly illustrated in FIG. 1.

Referring more closely to FIGS. 1 and 3, connector assembly 10 includes a generally annular collar 30. Collar 30 has opposed proximal and distal ends 32 and 34 respectively. Proximal end 32 of collar 30 may be configures or otherwise provided with a plurality of deflectable latches 36 having locking portions 37 dimensioned for locking engagement with an underside portion **24*b* associated with annular rim 24 of vial 12. One or more locking detents 40 can be provided on deflectable latches 36 intermediate the proximal and distal ends of the collar. Locking detents 40 feature a sloped portion 40*a* and an upper face portion 40*b*. Sloped portion 40*a* permit the locking detents to slide over rim 24 when collar assembly 10 is urged in the proximal direction, while upper face portion 40*b* engages underside portion 24*b* of the rim to prevent the collar assembly from re-assuming its distal-most position once urged towards its proximal-most position. Portions of collar 30 between proximal and distal ends 32 and 34 include an upstanding annular wall 38 defining a well 39 having a shoulder 39*a***.

Figure 2:
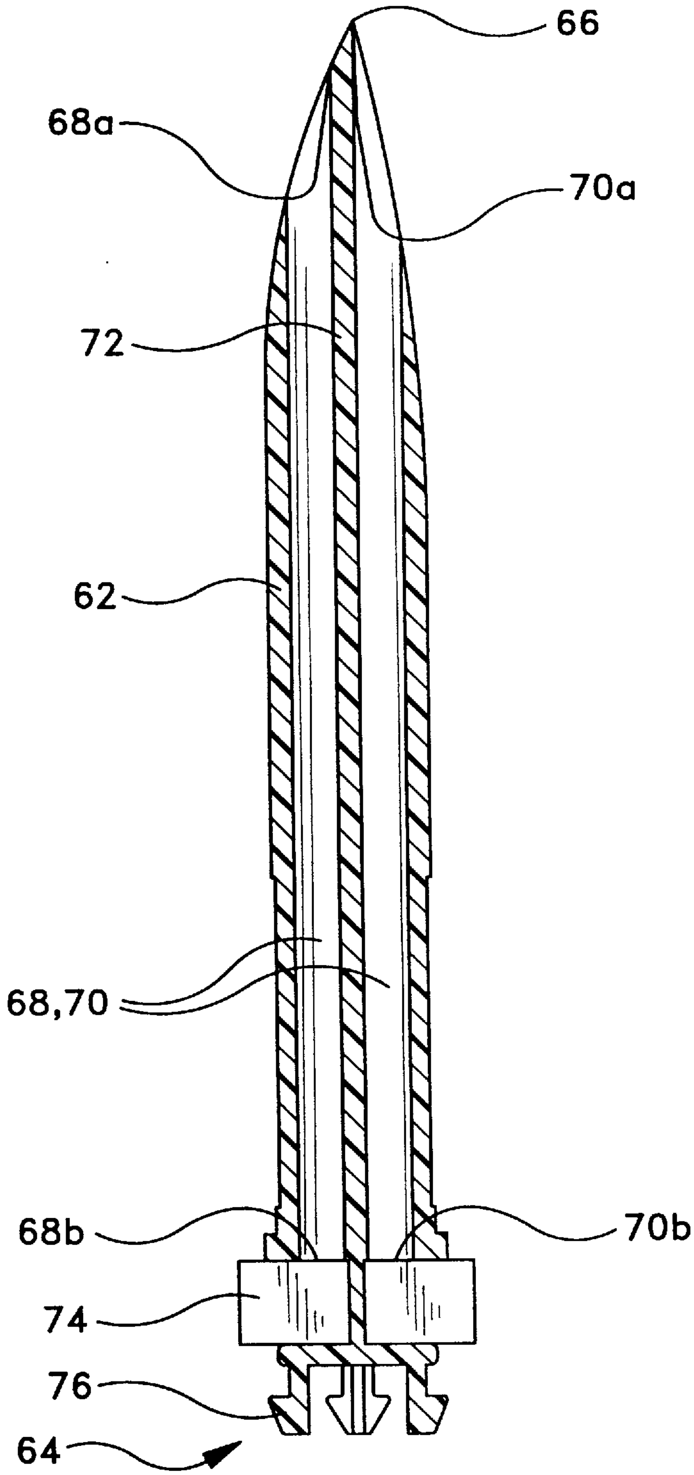
FIG. 2 is a cross-sectional view of a spike used in conjunction with the connector assembly of FIG. 1.

Connector assembly 10 further includes a way to transfer fluid between vial 12 and a source of solvent such as container source "B". As illustrated in the Figures, one way to transfer fluid is to provide connector assembly 10 with a fluid transfer tube such as a tubular spike 62. Referring most closely to FIGS. 1–3, spike 62, which can be molded from a thermoplastic material, includes an elongate structure having a proximal end 64, a pointed distal end 66 and a pair of axially extending passages 68 and 70 extending therethrough and separated from one another by a septum 72. Spike 62 can be affixed, in a concentric manner, to a receptacle 45 formed within collar 30. Receptacle 45 includes an outer wall 46 having a diameter "b" at least equal to, if not slightly less than, diameter "a" of the neck of vial 12 such that spike 62 is free to travel proximally and distally within vial neck 20 as collar 30 is urged between its distal-most and proximal-most positions.

Pointed distal end 66 is configured to puncture sealing portion "A" of the container source of solvent. Passages 68 and 70 have open axial termini **68*a*, 70*a* near pointed distal end 66. Axial termini 68*a*, 70*a* are placed at differing axial locations, or levels, along the elongate structure of the spike for substantially eliminating any possibility of both passages being obstructed by structure in either the vial 12 or container source "B" with which connector assembly 10 may communicate. Passages 68, 70 extend between their respective axial termini 68*a*, 70*a* and respective apertures 68*b*, 70*b* located near proximal end 64. As also seen, a plurality of vanes 74 may be disposed on spike 62 intermediate apertures 68*b*, 70*b* and proximal end 64**.

Connector assembly 10 provides a way to seal vial 10 and, particularly, drug 26 in a sterile manner. To this end, referring to principally to FIGS. 1–3, the connector assembly includes a stopper 44 and a secondary seal 48. Stopper 44 is grippingly engaged on fingers 76 disposed at the proximal end 64 of spike 62. Stopper 44 is spaced away from apertures **68*b*, 70*b* by vanes 74 so as to provide a fluid path permitting fluid flow into and out of apertures 68*b*, 70*b*. Stopper 44 is dimensioned for sliding fluid tight engagement with interior surfaces of neck 20 of vial 12. The relative dimensions of stopper 44, spike 62 and/or collar 30 can be configured such that stopper 44 will be in sealing engagement with neck 20 of the vial when collar 30 is in a distal-most position (FIG. 4) but will be disposed away from neck 20 and disposed towards the interior of vial 12 when collar 30 is in a proximal-most position (FIG. 5) so as to permit fluid flow between the interior of the vial and apertures 68***b*, 70*b*. It can be also provided that a distal portion 47 of stopper 44 seal a proximal end 21 of vial neck 20 when collar 30 is urged distally from its proximal-most position towards a secondary position (FIG. 6) intermediate the distal-most and proximal-most positions of the collar.

As seen further, connector assembly 10 includes a secondary seal 48. Seal 48 may be fitted about spike 62 between a base portion 46*a* associated with outer wall 46 of the receptacle and against a distal surface of vanes 74. Secondary seal 48 includes an outside diameter approximately equal to or slightly greater than inside diameter "a" of neck 20 on vial 12. The dimensions of secondary seal 48, spike 62 and/or collar 30 can be configured such that secondary seal 48 remains in sealing engagement with neck 20 of the vial irrespective of the position of collar 30 (FIGS. 4–6) relative to the neck of vial 12. The dimensions or shape associated with secondary seal 48, vanes 74, collar 30 and/or spike 62 can further be chosen such that secondary seal 48 hermetically isolates apertures 68*b*, 70*b* from the neck of the vial.

Figure 6:
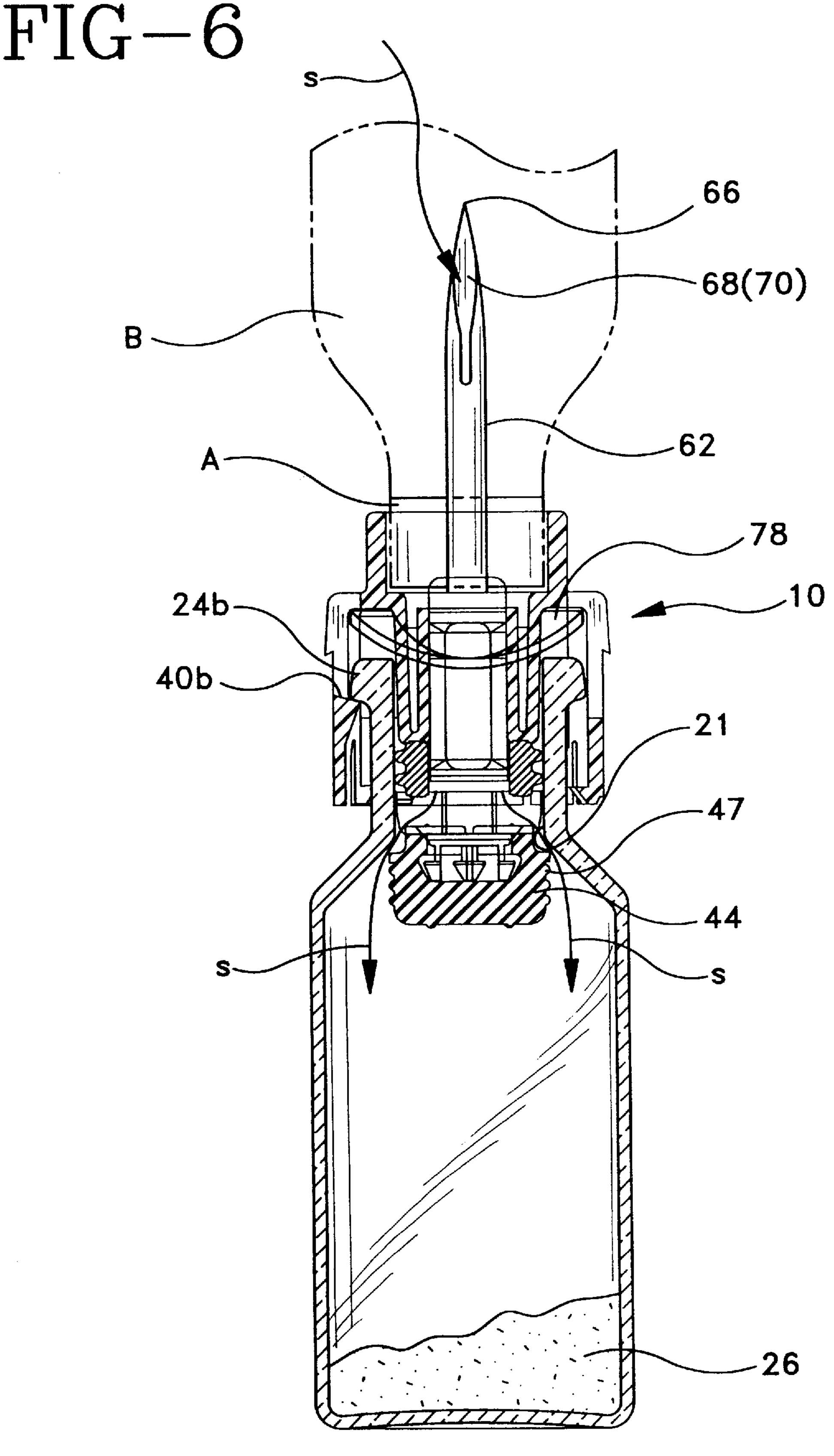
FIG. 6 is a cross-sectional view illustrating the connector assembly urged distally, after activation to the proximal-most position, to compensate for any surface tension or pressure differences between the vial and the source of solvent so as to initiate flow between the source of solvent and the vial.
Figure 7:
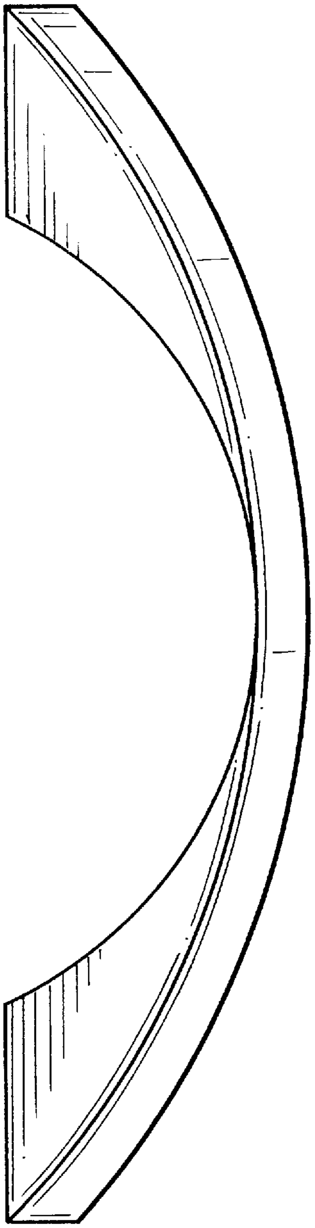
FIG. 7 is a partial cross-sectional view of a spring utilizable between the vial and the collar of the connector assembly to urge the collar assembly distally after reaching its proximal-most position.

If desired, a spring 78 may be provided with the connector assembly to assist in urging the connector assembly distally from its proximal-most position towards its intermediate position. As illustrated in FIGS. 4–7, spring 78 may assume an arcuate shape and can be formed from any suitable material such as ABS, POM, or any thermoplastic exhibiting desired elasticity characteristics. Spring 78 can be placed between rim 24 of the vial and the shoulder 39*a* of well 39 in a manner such that as connector assembly 30 is urged towards its proximal-most position, compressive forces imparted unto spring 78 can assist the user in deflecting the connector assembly distally towards its intermediate position (FIG. 6).

A protective cap 90 is provided about collar 30 to protect the connector assembly prior to use. Protective cap 90 may feature a sill 92 dimensioned to engage vial 12, such as at shoulder 18 or at side wall 16. If desired, connector assembly 10 may further include a safety shield 86, as shown in FIG. 1, which is releasably engaged around outer circumferential portions of collar 30 and dimensioned for further protectively enclosing spike 62. If also desired, a tamper evident seal (not shown) can be provided at the interface between sill 92 and the vial.

Figure 4:
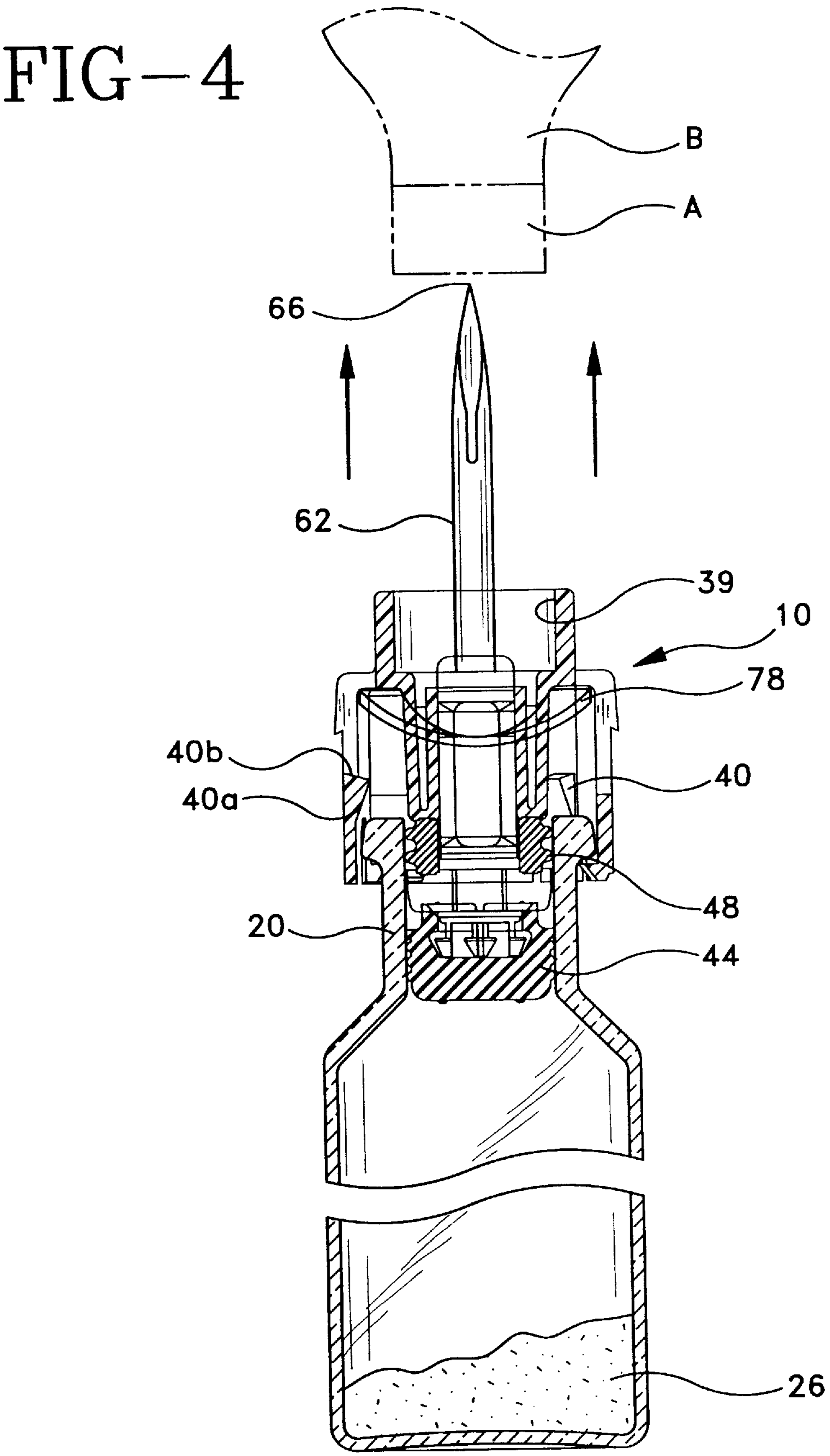
FIG. 4 is a cross-sectional view illustrating the connector assembly in a distal-most position relative to the neck of the vial, prior to activation by a user.
Figure 5:
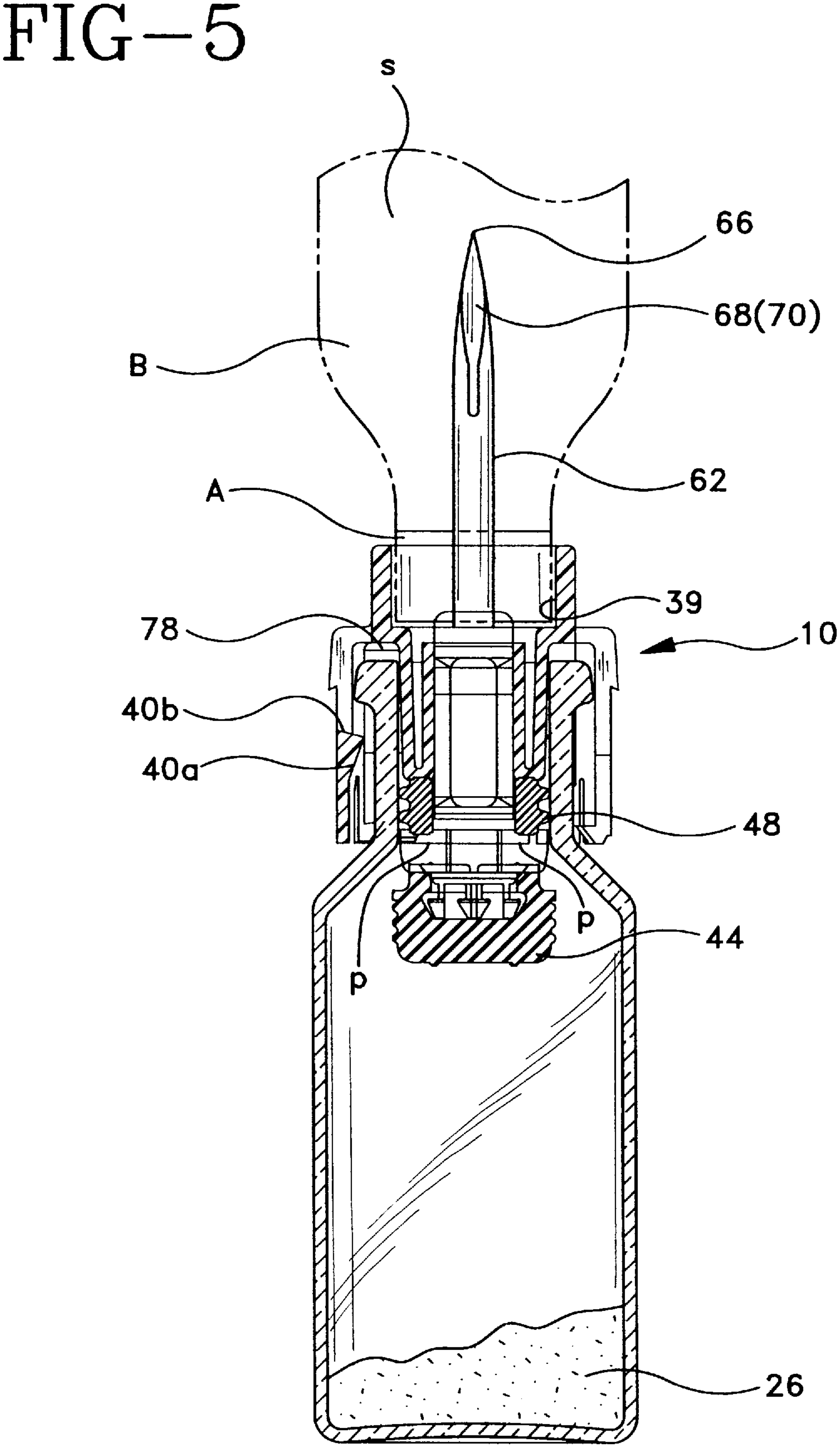
FIG. 5 is a cross-sectional view illustrating the connector assembly in a proximal-most position relative to the neck of the vial, subsequent to activation by a user.

Connector assembly 10 is employed by initially removing cap 90 and, if provided, safety shield 86. Vial 12, with connector assembly 10 mounted thereto, is urged toward container "B" to access solvent "S" held therein. FIG. 4 illustrates that as vial 12 is urged toward container "B", connector assembly 10 in its distal-most position relative to vial neck 20. Both stopper 44 and secondary seal 48 are engaged with vial neck 20. Sloped portions 40*a* of locking detents 40 rest against vial rim 24, while locking portions 37 of deflectable latches 36 engage underside portion 24*b* of the rim; in this manner, the collar may be held in its distal-most position until it is desired to activate the unit.

Continued force exerted on vial 12 will cause sealing portion "A" of container "B" to approach well 39, such that pointed distal tip 66 of spike 62 will pierce sealing portion "A", putting at least one of axial termini 68*a*, 70*a* in fluid communication with solvent "S". Frictional forces between sealing portion "A" and the spike and/or forces exerted by sealing portion "A" or container "B" onto distal end 34 of collar 30 will urge the collar proximally towards the proximal-most position illustrated in FIG. 5. Sloped portions 40*a* will pass over rim 24, and at the same time, both stopper 44 and secondary seal 48 will be urged proximally in neck 20. Distal portion 47 of stopper 46 will clear proximal end 21 of vial neck 20 so as to open a fluid path "P" between apertures 68*b*, 70*b* and the interior of the vial. Simultaneously, if provided, spring 78 will become compressed between rim 24 and shoulder 39*a* of the collar. It will be seen that secondary seal 48 remains engaged in vial neck 20. Because apertures 68*b*, 70*b* can access only the interior of container "B" a closed system is presented, with secondary seal 48 acting to preserve a hermetic seal between the interior of the vial and the ambient environment.

Hence, the forces applied to vial 12 will place the interior of vial 12 in communication with solvent "S" held in rigid container "B". More particularly, fluid communication will be achieved through one of passages 68 or 70 of spike 62 via axial termini 68*a*, 70*a* and apertures 68*b*, 70*b*. However, as explained above, pressure conditions and surface tension may impede flow of solvent "S" through spike 62. This problem is overcome by connector assembly 10. More particularly, once the connector assembly has been activated towards its proximal-most position relative to the vial neck (FIG. 5), it may be urged in a distal direction so as to create pressure fluctuations between vial 12 and container "B" to initiate flow between them. In the absence of spring 78, a user can merely urge collar 30 in alternating distal and proximal directions so as to generate a series of fluctuations. Alternately, a user may employ the compressive forces imparted upon spring 78, permitting spring 78 to thrust shoulder 39*a* away from rim 24, causing collar 30 to move in a distal direction. The movement of collar 30 will cause a small corresponding movement of remaining portions of spike 62 relative to vial 12, as shown in FIG. 6. This small relative movement of spike 62 will vary volume sufficiently to cause a minor pressure change that will overcome surface tension and static pressure conditions that would otherwise impede flow of solvent. As a result, solvent "S" will flow through one of channels 68 or 70 of spike 62 and into vial 12 for mixture with drug 26.

Once drug 26 is fully reconstituted, it may be re-aspirated into container "B" for direct infusion into the patient. Alternately, sealing portion "A" is removed from well 39, and spike 62 can be inserted into an appropriate fitting associated with medical infusion apparatus to deliver the reconstituted drug to a patient.

The dimensions and/or placement of deflectable latches, stopper 44 and/or spike 62 relative to vial neck 20 can be chosen such that upper face portions 40*b* of locking detents 40 engage underside portion 24*b* of the rim when collar 30 has assumed an intermediate position between the proximal most and distal-most positions. Here also, it can be configured so that distal portion of stopper 47 will block proximal end 21 of the vial neck when collar 30 has assumed its intermediate position. In this way, apertures 68*b*, 70*b* are blocked from fluid access with the interior of vial 12, thereby resealing the assembly and preserving the sterility of drug 26 held within the vial. This is particularly advantageous where multiple doses of a reconstituted drug are held within vial 12.

The skilled artisan will appreciate that the collar, spike and their associated components can be produced from materials known in the art, such as various thermoplastics. It will be apparent to the skilled artisan that the spike can be formed in a unitary manner with the collar; likewise, the spike can be separately formed and affixed to the collar, such as by welding, bonding or otherwise fitting the spike in a friction-tight manner with receptacle 45. While spring 78 can be formed in the manner previously described, it will also be apparent that substitute structure such as conventional metallic coil springs, elastomeric components or the like can also be used.

It will be appreciated and understood by those skilled in the art that further and additional forms of the invention may be devised without departing from the spirit and scope of the appended claims, the invention not being limited to the specific embodiments shown.

What is claimed is:

1. A connector assembly for a vial having a tubular neck, said connector assembly comprising:

a collar securely mounted around said tubular neck for sliding movement between a distal position and a proximal position relative to said tubular neck, and said collar including a proximal end and a distal end, a plurality of deflectable latches provided adjacent the proximal end of the collar, and at least one locking detent intermediate the proximal and distal ends of the collar, said plurality of deflectable latches engaged about the tubular neck of the vial;

a spike having a proximal end disposed in said vial, a distal end projecting from said vial and at least one channel extending therebetween, said spike being fixedly mounted to said collar for movement between said proximal and distal positions relative to said tubular neck, wherein upon said movement of said spike distally from said proximal position, said at least one locking detent is engageable with a rim portion of the vial to establish a third position of said spike intermediate said proximal and distal positions of said spike;

a stopper securely engaged to said proximal end of said spike and being slidably engaged in said tubular neck of said vial, said stopper being dimensioned for blocking said tubular neck when said spike is in said distal position and for being spaced from said neck when said spike is in said proximal position;

a secondary seal disposed on said spike and being slidably engaged in the tubular neck of said vial, said secondary seal positioned on said spike such that said secondary seal is disposed in said neck when said spike is in said proximal position;

whereby movement of said spike distally from said proximal position varies pressure sufficiently to permit efficient flow of fluid into said vial.

2. The connector assembly of claim 1, further comprising spring means for urging said spike distally from said proximal position for facilitating liquid flow through said channel of said spike and into said vial.

3. The connector assembly of claim 2, wherein said spring is unitary with spike.

4. The connector assembly of claim 1, further comprising a safety shield removably engaged over said collar and said spike.

5. The connector assembly of claim 1, wherein said stopper is positioned on said spike to block said tublular when said spike is in said third position.

6. The connector assembly of claim 1, further comprising an aperture in said spike communicating with said at least one channel, said aperture located on said spike intermediate said stopper and said secondary seal.

* * * * *